United States Patent
Shin et al.

(10) Patent No.: US 10,017,620 B2
(45) Date of Patent: Jul. 10, 2018

(54) METHOD FOR MANUFACTURING FIBROUS PARTICLES OF POLYLACTIC ACID RESIN, COLLOID COMPOSITION FOR FORMING FOAM SHEET, FOAM SHEET, AND METHOD FOR MANUFACTURING FOAM SHEET

(71) Applicant: LG Hausys, LTD., Seoul (KR)

(72) Inventors: Jun-Beom Shin, Suwon-si (KR); Sung-Yong Kang, Anyang-si (KR); Min-Hee Lee, Gunpo-si (KR); Hea-Won Kwon, Seoul (KR); Kyoung-Min Kang, Seoul (KR)

(73) Assignee: LG HAUSYS, LTD., Seoul (KR)

( * ) Notice: Subject to any disclaimer, the term of this patent is extended or adjusted under 35 U.S.C. 154(b) by 35 days.

(21) Appl. No.: 14/913,995

(22) PCT Filed: Aug. 29, 2014

(86) PCT No.: PCT/KR2014/008060
§ 371 (c)(1),
(2) Date: Feb. 24, 2016

(87) PCT Pub. No.: WO2015/030517
PCT Pub. Date: Mar. 5, 2015

(65) Prior Publication Data
US 2016/0222183 A1 Aug. 4, 2016

(30) Foreign Application Priority Data
Aug. 29, 2013 (KR) ........................ 10-2013-0103467

(51) Int. Cl.
| | | |
|---|---|---|
| *C08J 9/28* | (2006.01) | |
| *B29C 44/12* | (2006.01) | |
| *D01D 5/00* | (2006.01) | |
| *D01D 5/098* | (2006.01) | |
| *D01F 6/62* | (2006.01) | |
| *C08J 3/12* | (2006.01) | |
| *A61L 27/56* | (2006.01) | |
| *C08L 67/04* | (2006.01) | |

(52) U.S. Cl.
CPC ................ *C08J 9/28* (2013.01); *B29C 44/12* (2013.01); *C08J 3/122* (2013.01); *D01D 5/0023* (2013.01); *D01D 5/0069* (2013.01); *D01D 5/0985* (2013.01); *D01F 6/625* (2013.01); *A61L 27/56* (2013.01); *C08J 2201/05* (2013.01); *C08J 2201/0502* (2013.01); *C08J 2367/00* (2013.01); *C08J 2367/04* (2013.01); *C08L 67/04* (2013.01)

(58) Field of Classification Search
CPC ... A61L 27/56; C08L 67/04; C08J 9/28; C08J 3/122
See application file for complete search history.

(56) References Cited

U.S. PATENT DOCUMENTS

| | | | |
|---|---|---|---|
| 6,753,454 B1 * | 6/2004 | Smith ................... | A61L 15/225 602/41 |
| 2004/0146540 A1 * | 7/2004 | Ueda ...................... | A61K 8/025 424/401 |
| 2007/0190101 A1 * | 8/2007 | Yang ...................... | A61K 38/39 424/423 |

FOREIGN PATENT DOCUMENTS

| | | |
|---|---|---|
| CN | 1810877 A | 8/2006 |
| CN | 101035677 A | 9/2007 |
| CN | 101709534 A | 5/2010 |
| CN | 102884115 A | 1/2013 |
| CN | 103261299 A | 8/2013 |
| EP | 1683828 A2 | 7/2006 |
| JP | 07-216646 A | 8/1995 |
| JP | 2002-020526 A | 1/2002 |
| JP | 2012-025869 A | 2/2012 |
| JP | 2012-188560 A | 10/2012 |
| KR | 1020060086288 A | 7/2006 |
| KR | 10-2009-0008899 A | 1/2009 |
| KR | 100900251 B1 | 5/2009 |
| KR | 10201000015654 A | 2/2010 |
| KR | 101050338 B1 | 7/2011 |
| KR | 1020130067119 A | 6/2013 |
| WO | 2011100743 A2 | 8/2011 |

OTHER PUBLICATIONS

Shuxian Shi, "Preparation and Processing of Biomaterials", Chemical Industry Press, Aug. 31, 2009, pp. 296-300.
European Search Report for corresponding European Patent Application No. 14840397.5 dated Jan. 12, 2017.
Chinese Office Action for corresponding Chinese Patent Application No. 201480047647.8 dated Dec. 26, 2017.
International Search Report dated Dec. 8, 2014 corresponding to International Application No. PCT/KR2014/008060.
Japanese Office Action dated Apr. 27, 2018, issued in corresponding Japanese Application No. 2016-538856, citing the above reference(s).

* cited by examiner

*Primary Examiner* — Gregory Listvoyb
(74) *Attorney, Agent, or Firm* — Hauptman Ham, LLP

(57) ABSTRACT

The present invention relates to a colloid composition for forming a foam sheet including: polylactic acid resin particles having an average diameter of 1 μm to 100 μm obtained by pulverizing fibrous particles of a polylactic acid resin.

4 Claims, No Drawings

METHOD FOR MANUFACTURING FIBROUS PARTICLES OF POLYLACTIC ACID RESIN, COLLOID COMPOSITION FOR FORMING FOAM SHEET, FOAM SHEET, AND METHOD FOR MANUFACTURING FOAM SHEET

CROSS REFERENCE TO RELATED APPLICATION

This application claims the priority of Korean Patent Application No. 10-2013-0103467, filed on Aug. 29, 2013 in the KIPO (Korean Intellectual Property Office). Further, this application is the National Phase application of International Application No. PCT/KR2014/008060 filed Aug. 29, 2014, which designates the United States and was published in Korean.

TECHNICAL FIELD

The present invention provides a method for manufacturing fibrous particles of a polylactic acid resin, a colloid composition for forming a foam sheet, a foam sheet, and a method for manufacturing a foam sheet.

BACKGROUND ART

Products including a polylactic acid are produced through heat-processing several times. It has been reported that the polylactic acid is sensitive to heat and is hydrolyzed at a high temperature. Due to characteristic of the polylactic acid, the hydrolysis by heat in processing the products including the polylactic acid changes a molecular weight, which may also have an affect on the state of a finished product to be produced.

DISCLOSURE

Technical Problem

It is an aspect of the present invention to provide a colloid composition for forming a foam sheet, capable of manufacturing a foam sheet including a polylactic acid resin and having improved lifespan.

It is another aspect of the present invention to provide a method for manufacturing fibrous particles of a polylactic acid resin for preparing the colloid composition for forming a foam sheet.

It is still another aspect of the present invention to provide a foam sheet manufactured by using the colloid composition for forming a foam sheet.

It is still another aspect of the present invention to provide a method for manufacturing a foam sheet by using the colloid composition for forming a foam sheet.

Technical Solution

In accordance with one aspect of the present invention, a colloid composition for forming a foam sheet includes: polylactic acid resin particles having an average diameter of about 1 µm to about 100 µm obtained by pulverizing fibrous particles of a polylactic acid resin An aspect ratio of the fibrous particles of the polylactic acid resin may be about 20 to about 100.

An average diameter of a longitudinal section of the fibrous particles of the polylactic acid resin may be about 10 µm to about 300 µm.

In accordance with another aspect of the present invention, there is provided a foam sheet including a polylactic acid foam layer formed by foaming the colloid composition for forming a foam sheet as described above.

The polylactic acid resin particles may include the polylactic acid resin having a weight average molecular weight of about 100,000 to about 200,000.

In accordance with another aspect of the present invention, a method for manufacturing fibrous particles of a polylactic acid resin, includes: introducing a polylactic acid resin and forming a molten polylactic acid spray solution; and spraying the molten polylactic acid spray solution by a melt-spraying method and simultaneously cooling the molten polylactic acid spray solution to obtain fibrous particles of the polylactic acid resin.

The polylactic acid resin may be introduced into an extruder, transferred to a spray nozzle, and heated in the spray nozzle to form the molten polylactic acid spray solution.

The polylactic acid resin in a pellet form or in a powder form may be introduced into the extruder.

The molten polylactic acid spray solution may be introduced into the spray nozzle together with an air and then discharged.

The air that is injected into the spray nozzle may have a temperature of about 300° C. to about 500° C., a pressure of about 100 psi to about 1000 psi, and an injection speed of about 10 m/s to about 50 m/s.

The spray nozzle may have a temperature of about 200° C. to about 400° C.

The spray nozzle may have a pressure of about 10 psi to about 1000 psi.

The spray nozzle may have a diameter of about 0.5 mm to about 3.0 mm.

The molten polylactic acid spray solution may have a viscosity of about 1500 cp to about 3000 cp at about 250° C.

The molten polylactic acid spray solution may not include a plasticizer.

Melt electrostatic spray deposition (melt ESD) may be performed by applying voltage of about 10,000 V to about 50,000 V to the spray nozzle.

An aspect ratio of the fibrous particles of the polylactic acid resin may be about 20 to about 100.

A diameter of a longitudinal section of the fibrous particles of the polylactic acid resin may be about 10 µm to about 300 µm.

In accordance with still another aspect of the present invention, there is provided a method for manufacturing a foam sheet including a polylactic acid foam layer, including: preparing fibrous resin particles of a polylactic acid resin in which a diameter of a longitudinal section is about 10 µm to about 300 µm; pulverizing the fibrous resin particles of the polylactic acid resin to be polylactic acid resin particles having an average diameter of about 1 to about 100 µm; preparing a foaming resin composition as a colloid composition by mixing the pulverized polylactic acid resin particles with a solvent, and forming a layer by applying the foaming resin composition; and forming a polylactic acid foaming layer by foaming the layer formed from the foaming resin composition.

An aspect ratio of the fibrous particles of the polylactic acid resin may be about 20 to about 100.

Advantageous Effects

The foam sheet manufactured by using the fibrous particles of the polylactic acid resin may have excellent durability, surface characteristics, and improved lifespan.

BEST MODE

Hereinafter, exemplary embodiments of the present invention will be described in detail. However, the exemplary embodiments are only provided by way of example, and the present invention is not limited thereto, but may be defined by the scope of the appended claims.

In an exemplary embodiment of the present invention, the present invention provides a colloid composition for forming a foam sheet including polylactic acid resin particles having an average diameter of about 1 μm to about 100 μm obtained by pulverizing fibrous particles of a polylactic acid resin.

An aspect ratio of the fibrous particles of the polylactic acid resin may be about 20 to about 100. An average diameter of a longitudinal section of the fibrous particles of the polylactic acid resin may be about 10 μm to about 300 μm.

The fibrous particles of the polylactic acid resin having the aspect ratio may be manufactured by a melt-spraying method. Further, more uniform polylactic acid particles may be obtained by adding high-temperature and high-pressure air together to the spray nozzle at the time of performing the melt-spraying method. The melt-spraying method may be performed by a melt electrostatic spray deposition (melt ESD) in which voltage is applied at the time of performing the melt-spraying method.

The method for manufacturing fibrous particles of the polylactic acid resin is specifically described below. When the melt-spraying method is applied to manufacture the fibrous particles of the polylactic acid resin, there are advantages in that shapes of the particles may be easily controlled and the particles may have uniform size distribution.

According to another exemplary embodiment of the present invention, the present invention provides a method for manufacturing fibrous particles of a polylactic acid resin, including: introducing a the polylactic acid resin and forming a molten polylactic acid spray solution; and obtaining the fibrous particles of the polylactic acid resin by spraying the molten polylactic acid spray solution by a melt-spraying method while simultaneously cooling the molten polylactic acid spray solution.

The fibrous particles of the polylactic acid resin included in the above-described colloid composition for forming the foam sheet may be manufactured by the manufacturing method. Specifically, a diameter of a longitudinal section of the fibrous particles of the polylactic acid resin manufactured by the method may be about 10 μm to about 300 μm. In addition, specifically, an aspect ratio of the fibrous particles of the polylactic acid resin manufactured by the method may be about 20 to about 100.

In order to perform the melt-spraying method, first, the polylactic acid in a pellet form or a powder form is introduced into the extruder provided with the spray nozzle, and the polylactic acid in a pellet form or a powder form is molten in the spray nozzle at a high temperature to form the molten polylactic acid spray solution. Then, the molten polylactic acid spray solution is sprayed in a form of a high temperature of droplet having a micro size, wherein the spraying is performed in a cooling chamber, such that the droplet is simultaneously cooled at the time of spraying to thereby form a fibrous nano web of the polylactic acid resin.

The melt-spraying method may be selectively performed by the melt electrostatic spray deposition (melt ESD) in which voltage is applied to the spray nozzle.

The molten polylactic acid spray solution may be introduced into the spray nozzle together with an air and then discharged.

A size and a shape of the droplet of the molten polylactic acid spray solution to be discharged may be controlled by regulating a temperature, a pressure, and a speed of the air to be injected into the spray nozzle, and accordingly, the size of the particles of the polylactic acid resin to be finally formed may be controlled.

For example, the air that is injected into the spray nozzle may have a temperature of about 300° C. to about 500° C., the air that is injected into the spray nozzle may have a pressure of about 10 psi to about 1000 psi, and an injection speed of air may be about 10 m/s to about 50 m/s.

Processing conditions of the melt-spraying method are not specifically limited, but the melt-spraying method may be performed under known processing condition, for example, a pressure of the spray nozzle of about 100 psi to about 1000 psi.

It is provided that the melt-spraying method is performed at a temperature range at which the polylactic acid is molten. For example, the spray nozzle may have a temperature of about 200° C. to about 400° C.

Further, in order to form micro-sized particles of polylactic acid resin as described above, the spray nozzle may have a diameter of about 0.5 mm to about 3.0 mm. The diameter of the spray nozzle may be controlled so that the fibrous particles of the polylactic acid resin have the above-described diameter of the longitudinal section of the fibrous particles.

The melt-spraying method may be, for example, performed by a melt electrostatic spray deposition (melt ESD) in which voltage of about 10,000 V to about 50,000 V is applied to the spray nozzle.

According to viscosity of the spray solution, the shape of the particles of the polylactic acid resin to be formed by cooling the droplet may be determined. In order to form the fibrous particles, specifically, viscosity of the applying liquid may be about 1500 to about 3000 cp at about 250° C.

In order for the spray solution to have the viscosity in the above range, the spray solution may be easily prepared without separately using additives such as a plasticizer, and the like.

The spray solution may further include additives such as a melt strength reinforcing agent, a lubricant, a hydrolysis resistant agent, and the like, as needed.

The polylactic acid resin particles as particulates capable of forming colloid, may be formed by pulverizing the fibrous particles of the polylactic acid resin.

The method of pulverizing the fibrous particles of the polylactic acid resin is not specifically limited, but the fibrous particles of the polylactic acid resin may be pulverized as amorphous particulates by known pulverization methods. For example, the fibrous particles of the polylactic acid resin may be pulverized as fine particles by a disc refiner.

The pulverized polylactic acid resin particles may be used to manufacture a foam sheet.

The pulverized polylactic acid resin particles may form the colloid composition.

In an exemplary embodiment, a sol solution may be prepared by adding additives to the pulverized polylactic acid resin particles, followed by mixing.

A method of manufacturing the foam sheet by using the colloid composition is not limited to specific manufacturing methods, but the foam sheet may be manufactured by methods known in the art.

In an exemplary embodiment, the sol as the colloid composition formed as above may be prepared, and coated (sol-coated) on the substrate, thereby manufacturing a foam layer.

In still another exemplary embodiment of the present invention, the present invention provides the foam sheet including the foam layer formed by foaming the colloid composition.

In generally, the foam sheet formed by including the polylactic acid foam layer may be manufactured by various processes. For example, first, a polylactic acid resin in a pellet form is manufactured by kneading and extruding polylactic acid resin powder, and then, T-die extrusion, lamination, and foaming processes are performed. In order to manufacture the foam sheet by these processes, at least three or four heat processes are generally required.

However, it is known that since polylactic acid resin is hydrolyzed at a high temperature, it is sensitive to heat treatment. Due to properties of the polylactic acid resin, the foam sheet to which the polylactic acid resin is applied may have an affect on a molecular weight of the polylactic acid resin according to hydrolysis by heat in processing, which may cause deterioration of products.

Since the foam layer of the foam sheet is manufactured by foaming the colloid composition, the number of heat treatment processes which are generally required may be reduced to prevent deterioration of the polylactic acid by heat treatment, thereby more highly maintaining the molecular weight of the polylactic acid. As a result, the foam sheet may be formed as a polylactic acid foam having higher molecular weight, thereby improving durability.

Specifically, the foam sheet may include the polylactic acid resin having a weight average molecular weight of about 100,000 to about 200,000.

In still another exemplary embodiment of the present invention, the present invention provides a method for manufacturing a foam sheet capable of reducing the number of heat treatment processes by using the fibrous resin particles of the nano polylactic acid resin in manufacturing the foam sheet.

The method for manufacturing a foam sheet including a polylactic acid foam layer may include: obtaining fibrous resin particles of a polylactic acid resin in which a diameter of a longitudinal section is about 10 μm to about 300 μm; pulverizing the fibrous resin particles of the polylactic acid resin to be polylactic acid resin particles having an average diameter of 1 μm to 100 μm; preparing a foaming resin composition as a colloid composition by mixing the pulverized polylactic acid resin particles with a solvent, and forming a layer by applying the foaming resin composition; and forming a polylactic acid foaming layer by foaming the layer formed from the foaming resin composition.

The fibrous resin particles of the polylactic acid may be manufactured by melt electrostatic spray deposition (melt ESD) as described above.

In the foam layer formed as described above, nanoparticles of the polylactic acid resin are uniformly dispersed. Since the polylactic acid resin is present while being uniformly dispersed, the finally manufactured foam sheet may have improved surface characteristics and improved durability of the foam sheet.

The method for manufacturing the foam sheet reduces the number of heat treatment processes as compared to the generally known process for manufacturing the foam sheet, such that damage by the hydrolysis of the polylactic acid resin may be remarkably reduced, and accordingly, reduction of the molecular weight by the hydrolysis of the polylactic acid resin may be inhibited. Accordingly, the foam sheet manufactured by the method for manufacturing the foam sheet remarkably improves product deterioration by heat treatment processes, thereby improving lifespan.

In the foam sheet manufactured by the method for manufacturing the foam sheet, the molecular weight of the used polylactic acid resin may not be significantly reduced by hydrolysis, but may be maintained. For example, the foam sheet manufactured by the method for manufacturing the foam sheet may include the polylactic acid resin having a weight average molecular weight of about 100,000 to about 200,000.

Hereinafter, Examples and Comparative Examples of the present invention will be described. However, the following Examples are only provided as one exemplary embodiment of the present disclosure, and the present disclosure is not limited to the following Examples.

EXAMPLES

Example 1

Fibrous particles in which an average diameter of a longitudinal section is about 150 μm, and an aspect ratio is 50 were manufactured from a polylactic acid resin in a pellet form by melt electrostatic spray deposition (melt ESD). When the melt electrostatic spray deposition was performed, a spray nozzle had a temperature of 250° C., a pressure of 500 psi, a diameter of 1 mm, and an applied voltage to the spray nozzle was 20,000 V. The molten polylactic acid spray solution had a viscosity of 2200 cp at 230° C.

A web which is fibrous particles of the manufactured polylactic acid resin was pulverized as fine particles by a disc refiner to manufacture particles having an average diameter of 80 μm.

The manufactured polylactic acid particles were mixed with additives such as a plasticizer, a stabilizer, a lubricant, and the like, followed by stirring, thereby preparing a polylactic acid resin-containing sol. The prepared polylactic acid resin-containing sol was sol-gel coated on a substrate, followed by drying (foaming), thereby manufacturing a foam sheet sample having a thickness of about 0.5 mm.

Comparative Example 1

A polylactic acid resin-containing mixing composition was prepared by mixing the same polylactic acid resin in a pellet form as Example 1 with additives such as a plasticizer, a stabilizer, a lubricant, and the like. The polylactic acid resin-containing mixing composition was kneaded at 150° C. by a Banbury mixer, and primarily and secondarily mixed by a twin roll at 150° C. The prepared mixing raw materials were subjected to calendaring processing and foaming, thereby manufacturing a foam sheet sample having a thickness of 0.5 mm.

Evaluation

Experimental Example 1

Measure of Molecular Weight of Polylactic Acid

Weight average molecular weight of each of the foam sheet sample manufactured by Example 1 and Comparative Example 1 was measured by gel permeation chromatography (GPC) (e2695, Waters), and results thereof were shown in Table 1 below.

Experimental Example 2

Evaluation of Durability

Impact resistance strength of each of the foam sheet sample manufactured by Example 1 and Comparative Example 1 was measured in accordance with ASTM D256, and results thereof were shown in Table 1 below.

Experimental Example 3

Evaluation of Surface Characteristics

Surface characteristics of each of the foam sheet sample manufactured by Example 1 and Comparative Example 1 were visually observed, and results thereof were shown in Table 1. The evaluation criteria were visually determined according to five-point scale from five (5) point (Excellent) to one (1) point (Not Good: NG).

TABLE 1

| Classification | Polylactic acid particles before manufacturing sheet in Example 1 | Polylactic acid in foam sheet of Example 1 | Polylactic acid in foam sheet of Comparative Example 1 |
|---|---|---|---|
| Weight Average Molecular Weight | 150,000 | 120,000 | 80,000 |
| Impact Resistance Strength [kgf cm/cm] | — | 20 | 30 |
| Evaluation of Surface Characteristics | | Blocking: 5 points Haze phenomenon: 4 points | Blocking: 4 points Haze phenomenon: 3 points |

The invention claimed is:

1. A colloid composition for forming a foam sheet consist essentially:
   polylactic acid resin particles having an average diameter of 1 μm to 100 μm obtained by pulverizing fibrous particles of a polylactic acid resin,
   wherein an aspect ratio of the fibrous particles of the polylactic acid resin is 20 to 100.

2. The colloid composition for forming a foam sheet of claim 1, wherein an average diameter of a longitudinal section of the fibrous particles of the polylactic acid resin is 10 μm to 300 μm.

3. A foam sheet comprising a polylactic acid foam layer formed by foaming the colloid composition for forming a foam sheet of claim 1.

4. The foam sheet of claim 3, wherein the polylactic acid resin particles include the polylactic acid resin having a weight average molecular weight of 100,000 to 200,000.

* * * * *